United States Patent [19]

Champ

[11] Patent Number: 4,921,491
[45] Date of Patent: May 1, 1990

[54] DISPOSABLE NEEDLE SYSTEM WITH CHEMICAL DISINFECTANT MEANS

[76] Inventor: Raynido A. Champ, 4205 Cedar La. #7, Portsmouth, Va. 23703

[21] Appl. No.: 332,594

[22] Filed: Apr. 3, 1989

[51] Int. Cl.⁵ .............................................. A61M 5/32
[52] U.S. Cl. .................................. 604/199; 604/263; 128/919
[58] Field of Search .............................. 128/763–765, 128/770, 919; 604/192, 194, 197–199, 263, 265

[56] References Cited

U.S. PATENT DOCUMENTS

| | | | |
|---|---|---|---|
| 2,847,995 | 8/1958 | Adams | 128/214 |
| 3,354,881 | 11/1967 | Bloch | 128/215 |
| 3,485,239 | 12/1969 | Vanderbeck | 128/218 |
| 4,416,663 | 11/1983 | Hall | 604/199 |
| 4,693,708 | 9/1987 | Wanderer | 604/198 |
| 4,695,274 | 9/1987 | Fox | 604/198 |
| 4,702,738 | 10/1987 | Spencer | 604/198 |
| 4,725,267 | 2/1988 | Vaillancourt | 604/192 |
| 4,740,205 | 4/1988 | Seltzer | 604/192 |
| 4,747,829 | 5/1988 | Jacob | 604/110 |

Primary Examiner—Max Hindenburg
Attorney, Agent, or Firm—Wallace J. Nelson

[57] ABSTRACT

A disposable needle system employing chemical disinfecting mechanism is disclosed. Both ends 13,14 of the needle are enclosed in individual spring biased, retractable sleeves 32,52 telescopically received within respective colinear tubular housings that support the needle structure. In use, sleeves 32,52 are retracted to expose needle ends 13,14 for respective insertion into the vein of a patient and for collecting the blood in a tube 71 or syringe 90. After use, the sleeves are returned to original position to again cover the needle ends and protect the user and any subsequent handler from exposure to accidental needle punctures. An additional precaution involves a disinfectant solution being dispersed into the tubular housings via passageway 66 and vial 75. Vial 75 is retained in the tubular housing by the tapered enlarged nozzle 79 being locked in passageway 66 to give a visual indication that the needle system has been used to thereby prevent inadvertent reuse.

20 Claims, 2 Drawing Sheets

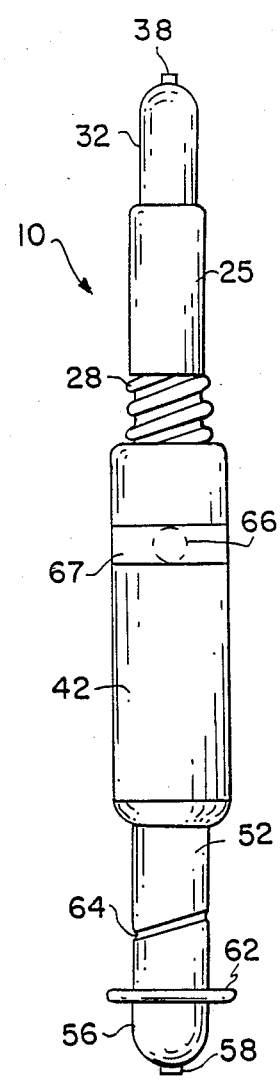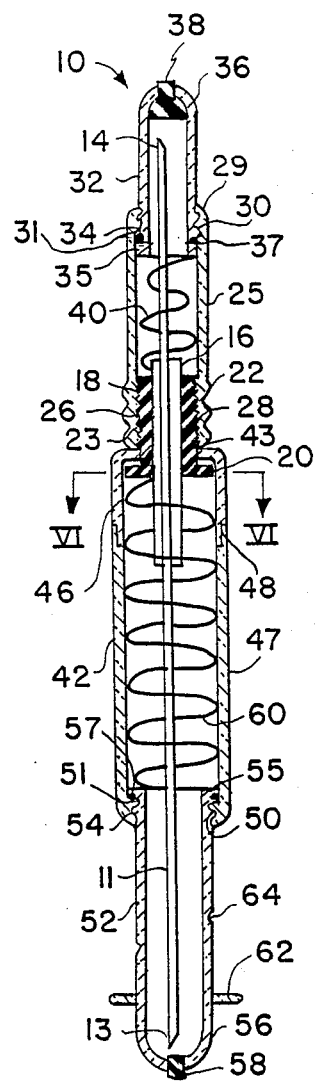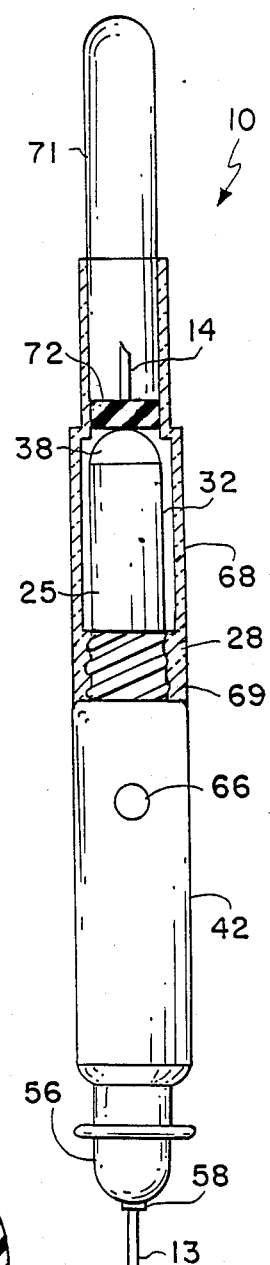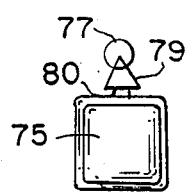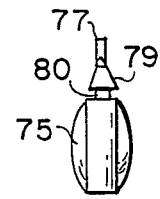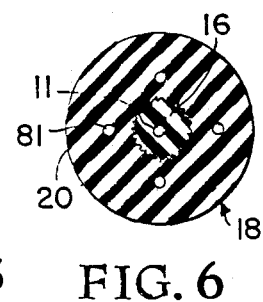
FIG. 1  FIG. 2  FIG. 3
FIG. 4  FIG. 5  FIG. 6

DISPOSABLE NEEDLE SYSTEM WITH CHEMICAL DISINFECTANT MEANS

FIELD OF THE INVENTION

This invention relates to disposable needle systems in general and relates specifically to a disposable needle system adapted to be contained within a closed protective housing and disinfected by a chemical disinfectant solution after use.

BACKGROUND OF THE INVENTION

Disposable needles and syringes are routinely used in hospital and other medical facilities for drawing blood and other body fluids from patients administering medications, and the like. For health and safety reasons and, as required by law in some jurisdictions, these disposable needles must be properly destroyed after use to prevent inadvertent reuse, accidental injury and possible exposure to transmittable diseases such as Hepatitis and AIDS. Presently, some reusable needles are cut or snipped from their syringes prior to being placed in collection boxes for disposal. Others are directly transferred, completely intact, to collection containers for disposal by incineration, or the like. In all cases, from the time the needle is used to the time that it is destroyed, medical personnel and clean-up crews are constantly at risk for accidental needle sticks. In the use of recappable needles, there is always a risk of inadvertent needle stick to the medical personnel doing the recapping. Once the needle has been deposited into the appropriate collection receptacle, higher risk exists for individuals responsible for ultimate disposal. Inadvertently, the caps fall off the disposed needles in the collection containers, leaving the contaminated needle points exposed. As the container is filled, exposed needles often protrude through the container opening. Therefore, any individual placing needles in this container risks getting stuck with the contaminated needles.

Traditional needle system have always been a health hazard risk to our medical personnel. Diseases such as Hepatitis and AIDS have brought to our attention the need to develop devices to better protect our medical personnel from these risks.

Although a number of solutions to this problem have been proposed there remains a need in the art for a more reliable system to reduce the possibility of inadvertent reuse and safe destruction of disposable needle systems.

It is therefore an object of the present invention to provide an improved disposable needle system.

A further object of the present invention is a disposable needle system that maintains the used needle within a protective housing that serves as a secured closed unit after needle use.

Another object of the present invention is a chemical solution disinfecting system that permits disinfection of a disposable needle system after use and prior to ultimate disposal thereof.

An additional object of the present invention is a disposable needle system that minimizes the chance for accidental needle stick injury to the user of the system prior to, during and after use thereof.

Another object of the present invention is the provision of visual indications that a disposable needle system has been used to avoid subsequent accidental reuse thereof.

SUMMARY OF THE INVENTION

According to the present invention, the foregoing and additional objects are attained by providing a disposable needle system including an elongated needle having a circumferentially disposed needle support about an intermediate length thereof and mounted in a first open end of a tubular housing. The needle has a first open end for insertion into the vein of a patient and a second open end for transferring the patient blood to a collection tube. Both ends of the needle are enclosed in individual, spring biased, retractable sleeves telescopically received within respective colinear tubular housings that also receive the needle support.

A blood tube holder connects to one of the tubular housings with the contained blood tube serving to retract one of the retractable sleeves to permit an end of the needle to be received by the blood tube. The other retractable sleeve is manually retracted against its spring to expose the other end of the needle for insertion into the vein of a patient. After withdrawal of the blood, the needle is removed from the patient and the manually retracted sleeve is moved forward to again cover that end of the needle. The blood tube and tube holder are then removed from the other needle end and the retracted spring biased sleeve again covers that end of the needle. Each retractable sleeve is provided with a rubber septum closure that is penetrated by the needle end when the sleeve is retracted. The rubber septum closes when the sleeve is extended over the needle end.

A transverse opening in the sidewall of the tubular housing permits the insertion of a tapered tip nozzle of a flexible vial to dispense a quantity of chemical disinfectant solution into the housing. The tapered tip construction causes the tip to lock within the transverse opening to thereby retain the vial in position and give visual indication that the needle system has been used. By shaking or agitating the needle system, the chemical solution contacts all of the needle and interior housing surfaces to disinfect or neutralize any contamination therein and prevent any accidental exposure to individuals subsequently handling the used system.

BRIEF DESCRIPTION OF THE DRAWINGS

A more complete appreciation of the invention and many of the attendant advantages thereof will be more readily apparent as the same becomes better understood by reference to the following detailed description when considered in reference to the accompanying drawings wherein:

FIG. 1 is a view of the disposable needle system of the present invention prior to use thereof;

FIG. 2 is a part sectional view of the disposable needle system shown in FIG. 1;

FIG. 3 is a part sectional view of the disposable needle system of the present invention in operative condition;

FIG. 4 is a front view of a vial containing a chemical disinfectant solution for disinfecting the disposable needle system shown in FIGS. 1-3;

FIG. 5 is a side view of the vial shown in FIG. 4;

FIG. 6 is a sectional view taken along line VI—VI of FIG. 2;

DETAILED DESCRIPTION

Figure 7:
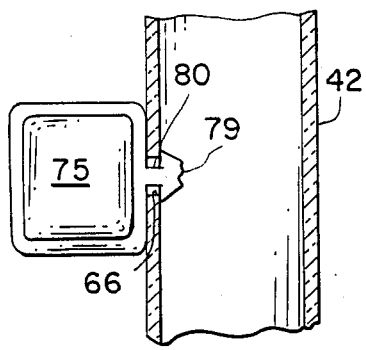
FIG. 7 is a part sectional view of a portion of a used disposable needle system of the present invention showing the chemical solution vial attached and giving visual indication that the system has been used.

Referring now to the drawings, and more particularly to FIGS. 1 and 2, the preferred embodiment of the disposable needle system of the present invention is shown and designated generally by reference numeral 10. Needle system 10 includes an elongated needle 11 formed of stainless steel or like material and having first and second sharp open ends, as designated by reference numerals 13,14. A plastic needle support member 16 is molded onto or otherwise fixedly attached to an intermediate length of needle 11. Needle support member 16 is fixedly secured within a centrally disposed bore (not designated) of a tubular insert 18. Tubular insert 18 is provided with an enlarged circumferential flange or "hat" section 20 with a shank section 22 integrally extending therefrom. Shank section 22 is provided with external threads 23 along the length thereof.

An elongated tubular barrel member 25, having an internal threaded section 26 at a first end thereof, is threadingly secured to the threaded shank 22. Tubular barrel member 25 is also provided with external threads 28 along a portion of its length at the first end thereof. The second open end 29 of barrel member 25 is provided with internal threads 30 over a minor portion of the length thereof. An annular shoulder 31 is provided within barrel 15 adjacent threads 30. A first retractable sleeve 32 has an open end thereof telescopically received within the second open end 29 of barrel member 25. External threads 34 are provided on the exterior circumferential surface of the open end of retractable sleeve 32. Threads 34 matingly engage threads 30 to assist in maintaining first retractable sleeve 32 in the maximum extended telescoped position shown in FIG. 2. An annular end flange 35 merges with threads 34 and abuts shoulder 31 when retractable sleeve 32 is in the maximum extended position shown in FIG. 2. An O-ring seal 37 is carried by annular flange 35 and bears against shoulder 31 to effect a seal therebetween and prevent any fluid leakage between these parts.

Sleeve 32 is also provided with a rounded end 36. End 36 has a central aperture therethrough closed by a rubber septum 38. Rubber septum 38 is of extra thickness and extends within an area of barrel 32 and is adapted to be pierced by second open end 14 of needle 11 when first retractable sleeve 32 is telescopically moved to retracted position within elongated tubular barrel 25, as will be further explained hereinafter. A spiral spring 40 is disposed within tubular barrel 24 surrounding needle 11 and having the ends thereof bearing, respectively, against the open end of retractable sleeve 32 and tubular insert 18 to assist in maintaining retractable sleeve 32 in maximum extended, telescoped position relative to barrel 25.

Hat section 20 of tubular insert 18 is disposed within an elongated tubular housing 42 and rests against the inside surface of a first open end 43 thereof. The shank section 22 of tubular insert 18 extends through first open end 43 and threaded barrel 25, secured to shank section 22, rests against the exterior in turned shoulder of first open end 43 of elongated tubular housing 42. An O-ring rubber seal (not shown) is provided at the end of threaded barrel 25 and bears against tubular housing 42 to prevent any exterior fluid leakage between these components. As shown, elongated tubular housing 42 is constructed of two tubular sections 46,47 joined together by threaded or other conventional connection 48. Elongated tubular housing 42 is provided with a second open end having internal threads 50 disposed therein. A second retractable sleeve 52 has an open end thereof telescopically received within the second open end of tubular housing 42.

Threads 54 are provided on the exterior circumferential surface of the open end of second retractable sleeve 52. Threads 54 matingly engage threads 50 to assist in maintaining second retractable sleeve 52 in the maximum extended telescoped position, shown in FIG. 2. An annular shoulder 51 is provided within tubular housing 42 adjacent threads 50. An annular flange 55 merges into threads 54 and abuts shoulder 51 when second retractable sleeve 52 is in the maximum extended position shown in FIG. 2. An O-ring rubber seal 57 is carried by annular flange 55 and bears against shoulder 51 to effect a fluid seal therebetween and prevent any fluid leakage between these parts.

Sleeve 52 is also provided with a rounded end 56. Rounded end has a central aperture therethrough that is closed by a rubber septum 58. Septum 58 is pierced by first open end 13 of needle 11 when second retractable sleeve 52 is telescopically moved to retracted position within tubular housing 42, as will be further explained hereinafter.

A spiral spring 60 is disposed within tubular housing 42 surrounding needle 11 and having the ends thereof bearing, respectively, against the open end of second retractable sleeve 52 and hat section 20 of tubular insert 18 to assist in maintaining sleeve 52 in maximum extended telescoped position relative to tubular housing 42.

An annular ring member 62 is integrally attached to, and circumferentially disposed about, second retractable sleeve 52 in spaced adjacency to the closed rounded end 56 thereof. Ring member serves as a handle or gripping surface to assist in manual rotation and telescoping retraction of sleeve 52 to cause penetration of septum 58 by needle end 13 and permit insertion of needle 11 into the vein of a patient.

A circumferential spiral groove 64 is provided on the exterior surface of second retractable sleeve 52 in spaced adjacency to annular ring member 62. Circumferential groove 64 serves to receive one or a portion of one of the spiral lands of threads 50 when sleeve 52 is moved to retracted position and assists in maintaining sleeve 52 in the telescoped retracted position within tubular housing 42.

A transverse opening 66 (FIG. 1) is provided through a sidewall of tubular housing 42 for administering a chemical disinfectant solution therethrough, as will be further explained hereinafter.

Referring now more particularly to FIG. 3, needle system 10 is shown in operative condition for obtaining a blood sample from a patient. As shown therein, a tubular blood tube holder 68 is threadingly secured to tubular barrel 25 via internal threads 69 in tube holder 68 mating with external threads 28 on barrel 25. Prior to attaching tube holder 68, first retractable sleeve 32 is retracted sufficiently, by manual rotation, to disengage threads 28 and 34. This retraction of sleeve 32 is adequate to cause needle tip 14 to move partially through septum 38 to the position thereof illustrated in FIG. 8. A blood collection tube 71, having a soft rubber seal 72 thereon, is then slidably inserted into the open end of tube holder 68 and retained therein by the circumference of rubber seal 72 frictionally engaging the interior of tube holder 68. Tube 71 is a conventional evacuated blood collection tube and is inserted within tube holder 68 such that rubber seal 72 engages the rounded end 36 of first retractable sleeve 32.

Manual pressure on blood collection tube 71 overcomes the force of spring 40, to effect relative telescopic movement of retractable sleeve 32 into barrel 25 until second end 14 of needle 11 completely pierces through septum 38 and engages or partially pierces rubber seal 72, but not to the point that needle end 14 enters the vacuum area of blood collection tube 71. The frictional contact of seal 72 against the interior wall of tube holder 68 is adequate to maintain spring 40 compressed and retain needle end 14 in position just short of entry into blood collection tube 71.

Prior to complete insertion of a blood collection tube 71 into holder 68, ring 62 is grasped and second retractable sleeve 52 is manually rotated against the force of spring 60 to separate threaded area 50,54. Manual force is then exerted on ring 62 to slidably and telescopically retract sleeve 52 into tubular housing 42 until spiral groove 64 thereon engages a portion of one of the lands of threads 50. This engagement of groove 64 with thread 50 serves to aid the retention of sleeve 52 in the retracted position. When retracted, and as shown in FIG. 3, first open end 13 of needle 11 pierces septum 58 and is exposed for insertion into a vein of a patient to acquire a blood sample.

After the insertion of needle end 13 into the vein of a patient, additional manual pressure is applied to blood collection tube 71 to cause it to be completely inserted within holder 68 to the position thereof as shown in FIG. 3. In this position the vacuum within tube 71 serves to "draw" the blood sample from the patient through needle into tube 71. The pressure exerted on sleeve 32 by blood collection tube 71 causes sleeve 32 to telescopically retract within tubular barrel 25 against the pressure of spring 40. After blood collection tube 71 is filled with blood it may be removed and replaced by another blood collection tube without removing needle end 13 from the patient. Upon removal of blood collection tube 71 from holder 68, spiral spring 40 forces first slidable sleeve 32 back to the position thereof shown in FIG. 8 where needle end 14 is retained within thick septum 38. This retention of needle end 14 within septum 38 effectively seals needle end 14 and prevents any blood leakage to the outside or inside of first retractable sleeve 32 during this procedure. A new blood collection tube 71 may then be inserted into holder 68 and another blood sample obtained. This procedure is repeated until the desired number of blood samples are collected and needle end 13 is then removed from the patient's vein. As the needle end 13 is removed from the patient, annular ring 62 is grasped by the operator to manually and rotatatively extend second retractable sleeve 52 back to the position shown in FIG. 2. In this position, threads 50,54 again lock sleeve 52 in maximum extended telescoped position relative to tubular housing 42 and needle end 13 is again covered. Rubber septum 58 sealingly closes the opening made by needle end 13 as is well known in the art.

Figures 8, 9, 10:
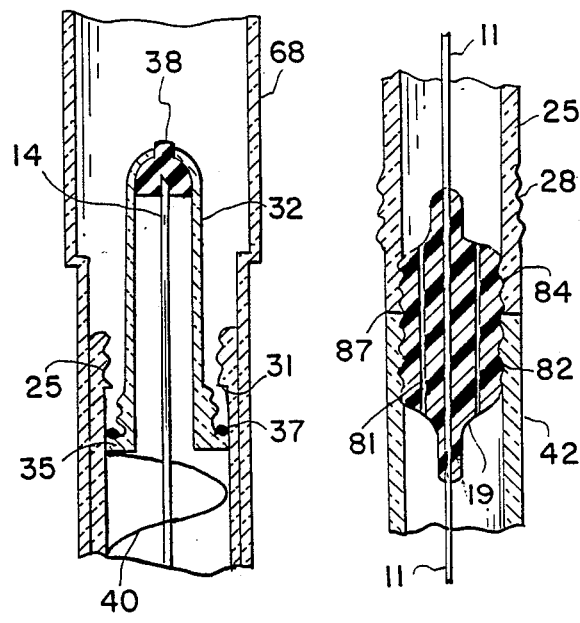
FIG. 8 is a partial view of the assembly shown in FIG. 3 when a blood tube is withdrawn from the tube holder and prior to insertion of another blood tube.
FIG. 9 is a view of an alternate embodiment of the disposable needle system of the present invention; and, FIG. 10 is a view of the disposable needle system shown in FIGS. 1 and 2 when employing a specific syringe to collect blood in lieu of the blood collection tube employed in FIG. 3.

Tube holder 68 is then threadingly removed from barrel 25, spiral spring 40 having already effected telescopic movement of first retractable sleeve 32 back to the position thereof shown in FIG. 8. Manual rotation is applied to sleeve 32 to again cause threads 30,34 to lock the sleeve in maximum extended position relative to barrel 25 and needle end 14 is again covered. Rubber septum 38 sealingly closes the opening made by needle end 14 therein. Disposable needle assembly 10 is now ready for disposal and destruction. However, in order to minimize or eliminate accidental reuse thereof and to minimize or prevent accidental contamination to individuals, further action is needed.

Referring now more particularly to FIGS. 4 and 5, a flexible plastic vial 75 containing a chemical disinfectant solution is provided with each disposable needle system 10. Vial 75 is provided with a pliant dispensing nozzle 79 having a break away tip 77 thereon. Nozzle 79 tapers from a pointed tip section to an enlarged base connected to vial 75 by a reduced diameter section 80. In operation, (note FIGS. 1 and 7), after removal of break away tip 77, the open pointed end of dispensing nozzle 79 is inserted into transverse opening 66 of housing 42. The enlarged end of pliant nozzle 79 has a diameter slightly larger than that of opening 66 and, when forced into opening 66, the pliant nozzle 79 is compressed slightly. When the reduced diameter area 80 is reached, the pressed enlarged area reverts back to normal size and prevents subsequent removal from opening 66. Vial 75 is then squeezed to expel the contents thereof into housing 42. Disposable needle assembly 10 is then manually agitated to distribute the expelled chemical solution over all surfaces within the confines of assembly 10. The volume of disinfectant contained within and dispensed from vial 75 is approximately one-half of the volume of the open space within needle system 10. Since vial 75 cannot be removed from tubular housing 42, the presence of the connected vial gives visual indication that needle system 10 has been used and should be destroyed without further use.

As shown more clearly in FIG. 6, tubular insert 18 is provided with a plurality of through openings 81 extending through enlarged section 20 and shank portion 22 thereof. Openings 81 serve to provide fluid communication between tubular barrel 25 and tubular housing 42 and ensure that the chemical disinfectant solution reaches all internal surfaces of disposable needle assembly 10 during agitation thereof.

Disposable needle system 10 and vial 75, as received by the user, are packaged in sterilized condition in a single sealed container. In addition, transverse hole 66 in tubular housing 42 may be covered with a removable, porous, pressure sensitive material 67 that permits sterilization gases to pass therethrough but maintains the sterile condition for the contained components. This pressure sensitive material 67 is removed before insertion of nozzle 79 of vial 75 into opening 66.

Any suitable disinfectant chemical solution may be employed in vial 75. Chemical solutions of this type include, but are not limited to, various chloride solutions, such as sodium hypochlorite (household bleach strength), and the like. Any suitable bacteriocide, virucide, bacteriostatic or virustatic solution that proves adequate for decontamination or disinfection of the used needle system is considered applicable for practice of the present invention.

Referring now more particularly to FIG. 9, an alternate embodiment of the present invention is shown employing a modified tubular needle support and holder 19. Needle holder 19 is of unitary construction and is molded directly to, and surrounds, the intermediate area of needle 11. Needle holder 19 replaces needle support member 16 and tubular insert 18 as employed in the embodiment of FIGS. 1-3 and is provided with external annular threads 82 along the entire length thereof. In this embodiment elongated tubular barrel 25 extends beyond external threads 28 thereon to include an internally threaded extension 84 that threadingly engages threads 82 on needle support and holder 19. Tubular housing 42 also is modified to provide the first open end thereof with an internally threaded area 84 that threadingly engages threads 82 on needle support and holder 19. An annular rubber washer 87 is disposed around needle support and holder 19 to engage both the threaded end 84 of tubular barrel 25 and the threaded end 86 of tubular housing 42 and form a fluid tight seal therebetween. Needle support and holder 19 is provided with a plurality of through openings 81 that perform the same function as that described for openings 81 in tubular insert 18.

Referring now more particularly to FIG. 10, a modification to the blood collection system of FIG. 3 is shown. In this embodiment, the holder 68 and evacuated blood collection tube 71 are replaced with a syringe 90 that serves as the blood collection device. Syringe 90 is provided with a retractable plunger 91 therein and includes an internally threaded shank 93 that is threadingly attached to external threads 28 on barrel 25. A rubber septum 94 is provided in shank 93 to seal syringe 90 at the shank end. When a patient's vein is too small or otherwise proves inadequate to supply blood to the evacuated blood collection tube 71, additional suction force is sometimes needed to obtain the blood sample. In this situation syringe 90 is employed, as illustrated, and as plunger 91 is withdrawn therein, the suction force generated will draw the needed blood sample through the needle system. Once an adequate blood sample is obtained, shank 93 is unthreaded from barrel 25 and first retractable sleeve 32 moved by spring 40 to the position as shown in FIG. 8 to seal needle end 14, as in the previously described embodiments. The remaining disposal steps are the same as that described hereinbefore. Syringe 90 may also be employed to administer medications into the patient's blood stream through needle assembly 10, if so desired.

Although the invention has been described relative to specific embodiments thereof, it is not intended to be so limited. There are numerous modifications and variations of the present invention that will be readily apparent to those skilled in the art in the light of the above teachings. For example, no specific materials have been mentioned for construction of the various components of the present invention, it being understood that the various components of the disposable needle system described herein may be constructed of conventional plastic materials now used for similar systems and including polyethylene, polypropylone, and the like. Also, needle support 16, tubular insert 18, as well as needle support and holder 19 may be constructed of plastics or a hard rubber, if so desired. Where connections are made, the use of heat sealing, adhesives, and the like conventional connections are considered applicable to the present invention, in addition to, or in lieu of the O-ring and flat rubber seals described herein. Spiral springs 40 and 60, as well as needle 11, are constructed of stainless steel, or like material.

The specific design described and illustrated for the various components may also be altered without departing from the spirit and scope of the present invention. In this respect, needle support member 16 need not be circular in cross-section but could be square or of other shapes with tubular insert 18 being correspondingly constructed to receive this changed cross-sectional area. Also, needle support member 16 and tubular insert 18, in the embodiment of FIGS. 1-8, could be a unitary structure and molded directly about needle 11 as that described for the embodiment of FIG. 9, if so desired, without departing from the teachings of the present invention. Tubular housing 42 need not be formed of two tubular sections, as described, but could be formed of a single tubular section with an end cap being provided for the second open end thereof, if so desired. Further, the threaded locking structure between the slidable sleeves and tubular barrel and tubular housing threads, could include additional threads, or other temporary or releasable locking structure could be substituted therefor, without departing from the spirit or scope of the present invention.

These and other modifications and variations of the present invention will be readily apparent to those skilled in the art in the light of the above teachings.

It is therefore to be understood that, within the scope of the appended claims, the invention may be practiced other than as specifically described.

What is claimed as new and desired to be secured by Letters Patent of the United States is:

1. A disposable needle system for use by an operator in obtaining blood from a patient comprising, in combination:
    needle means having a first open end for insertion into the vein of a patient and having a second open end for transferring the patient blood to a collection device,
    means for protecting the operator from accidental injury and contamination during and after use of said disposable needle system, and
    chemical disinfectant means connectable to said needle system after use to disinfect said needle means and prevent subsequent accidental contamination during and after disposal of said needle system.

2. The disposable needle system of claim 1 including:
    a needle support member integrally attached to and disposed between the ends of said needle means,
    a tubular housing having a first and a second open end,
    said needle support member being fixedly secured within said first open end of said tubular housing such that said first open end of said needle means for insertion into the vein of a patient extends from said second end of said tubular housing and said second open end of said needle means for transferring the patient blood to a collection device extends from said first end of said tubular housing, and
    protective retractable sleeve means disposed over both said first and said second open ends of said needle means.

3. The disposable needle system of claim 2 including:
    said needle support member being an elongated cylindrical structure and provided with external threads along the length thereof,
    said first end of said tubular housing being provided with an internally threaded area threadingly secured to the external threads, and along substantially half the length of, said needle support member, a tubular barrel having a first open end provided with an internal threaded area over a portion of the length thereof and secured to the external threads, and along substantially the remaining half length of, said needle support member, and an annular rubber seal member disposed about the circumference of said needle support member between, and in sealing contact with, said tubular housing and said tubular barrel.

4. The disposable needle system of claim 2 including: said needle support member having a portion thereof extending from said first open end of said tubular housing, a tubular barrel having a first open end colinearly fixed in contacting relationship to said first open end of said tubular housing and disposed in spaced circumferential relationship about a length of said portion of said needle support member, and said protective retractable sleeve means including
  (a) a first retractable sleeve having an open end and a closed end being telescopically received in a second open end of said tubular barrel and disposed in spaced relationship to and surrounding said second open end of said needle means, and
  a second retractable sleeve having an open and a closed end being telescopically received in said second open end of said tubular housing and disposed in spaced relationship to and surrounding said first open end of said needle means.

5. The disposable needle system of claim 4 including a rubber septum closing said closed end of each said first and second retractable sleeves and adapted to be penetrated by said first and said second open ends of said needle means when said first and said second retractable sleeves are moved to respective retracted telescoped positions.

6. The disposable needle system of claim 4 including a tubular insert disposed in said first end of said tubular housing,
  said tubular insert having a central opening therethrough, said central opening receiving and retaining said needle support member therein,
  said tubular insert having an enlarged end disposed within said tubular housing and a reduced diameter shank portion extending through said first opening in said tubular housing,
  said shank portion having external threads extending the length thereof,
  said tubular barrel having internal threads disposed within a length of said first open end thereof and being threadingly secured to said shank portion of said tubular insert to colinearly attach said tubular barrel to and in abutting relationship with said first open end of said tubular housing.

7. The disposable needle system of claim 4 including an external threaded segment being also provided along a length of said first open end of said tubular barrel.

8. The disposable needle of claim 4 including at least one through opening extending through said tubular insert shank and said enlarged end, said at least one through opening being spaced from said central opening therethrough to provide fluid communication between said tubular housing and said tubular barrel.

9. The disposable needle system of claim 4 including spiral spring means disposed within said tubular barrel, said spiral spring means having one end in contact with said first retractable sleeve and one end in contact with said shank portion of said tubular insert and serving to normally bias said first retractable sleeve into maximum extended telescoped position within said tubular barrel.

10. The disposable needle system of claim 9 wherein said second open end of said tubular barrel is provided with internal threads along a portion of the length thereof and said open end of said first retractable sleeve is provided with external threads disposed along a portion of the length thereof and mating with said internal threads in said tubular barrel to assist in maintaining said first retractable sleeve in maximum extended telescoped position relative to said tubular barrel.

11. The disposable needle system of claim 4 including spiral spring means disposed within said tubular housing, said spiral spring means having one end in contact with said second retractable sleeve and one end in contact with said enlarged end of said tubular insert and serving to normally bias said second retractable sleeve into maximum extended telescoped position relative to said tubular housing.

12. The disposable needle system of claim 11 wherein said second end of said tubular housing is provided with internal threads disposed along a portion of the length thereof and said open end of said second retractable sleeve is provided with external threads disposed along a portion of the length thereof and mating with said internal threads in said tubular housing to assist in maintaining said second retractable sleeve in maximum extended telescoped position relative to said tubular housing.

13. The disposable needle system of claim 12 including a ring member integrally attached to and circumferentially disposed about said second retractable sleeve in spaced adjacency to said closed end thereof and serving to assist in manual rotative and telescopic retraction of said second retractable sleeve to cause said first end of said needle means to penetrate said rubber septum and expose said first end of said needle for drawing blood from a patient, a spiral circumferential groove provided on the exterior of said second retractable sleeve in spaced adjacency to said ring member and serving to receive at least a portion of a spiral land of the internal threads in said second open end of said tubular housing when said second retractable sleeve is moved to retracted position and serving to assist in maintaining said second retractable sleeve in telescoped retracted position within said tubular housing.

14. The disposable needle system of claim 4 including said tubular barrel being provided with an externally threaded area along a portion of the length of said first end thereof,
  a tubular blood tube holder having a portion of the length of a first open end thereof provided with an internally threaded area and being threadingly secured to the external threaded area of said tubular barrel,
  said tubular blood holder having a second open end extending beyond said first retractable sleeve, and
  said collection device being an evacuated blood collection tube provided with a soft rubber seal and slidably inserted and frictionally retained within said tubular blood tube holder to receive said second open end of said needle means and collect the blood from the patient.

15. The disposable needle system of claim 4 including said tubular barrel being provided with an externally threaded area along a portion of the length of said first end thereof,
- a syringe having a slidable and retractable plunger therein,
- a tubular shank integrally extending from said syringe,
- said tubular shank portion having an internal threaded area threadingly attached to the externally threaded area of said tubular barrel,
- a rubber septum sealing said threaded shank portion of said syringe,
- said rubber septum being penetrated by said second end of said needle means when said tubular shank portion is threadingly attached to said tubular barrel to thereby permit said syringe to draw and collect the blood from the patient.

16. The disposable needle system of claim 1 wherein said chemical disinfectant means for disinfecting said needle means includes:
- a transverse opening provided in a sidewall of said tubular housing,
- a vial of chemical disinfectant solution insertable into and adapted to be locked within said transverse opening for dispensing a quantity of chemical disinfectant solution within said disposable needle system for disinfection of the needle means and the inside of said tubular housing and said tubular barrel.

17. The disposable needle system of claim 16 wherein said vial of chemical disinfectant solution includes a pliant dispensing nozzle extending from said vial, a break-away tip on said dispensing nozzle for opening thereof prior to insertion of said nozzle into said transverse opening of said tubular housing and means on said dispensing nozzle for locking said vial to said tubular housing when said dispensing nozzle is inserted into said tubular housing.

18. The disposable needle system of claim 17 wherein said vial of chemical disinfectant solution is constructed of a flexible plastic material, said means on said dispensing nozzle for locking said vial to said tubular housing including said dispensing nozzle being provided with a pointed open end exposed when said break-away tip is removed, said pointed open end tapering to an enlarged end and a reduced diameter segment spaced from said pointed end and disposed aft of said enlarged end and serving to provide connection between said nozzle and said vial, said enlarged end of said pliant dispensing nozzle being of a slightly larger diameter than that of said transverse opening and whereby said pointed open end of said pliant nozzle is inserted into said transverse opening in said transverse opening of said tubular housing of adequate distance to force said enlarged end into said transverse opening and permit said reduced diameter segment to enter said transverse opening and said enlarged end of said pliant nozzle is thereby prevented from withdrawal from said transverse opening to thereby lock said vial to said tubular housing, and said chemical disinfectant solution is dispensed within said tubular housing by manually squeezing said vial to expel the contents thereof.

19. A method of sterilizing a disposable needle assembly after use to prevent subsequent accidental contamination by anyone handling the system after use and during disposable thereof wherein the needle assembly comprises a closed tubular body, save for a transverse opening in sidewall thereof, and including the steps of:
- providing a flexible plastic vial containing a chemical disinfectant solution and sealed by a break-away sealing tip on a nozzle thereof,
- breaking away the break-away sealing tip to expose an open tapered nozzle on the flexible plastic vial containing the sterilizing chemical solution, said tapered nozzle having an enlarged portion thereof slightly larger than the transverse opening in the sidewall of the disposable needle assembly and a reduced diameter segment between the enlarged portion and the vial,
- forcing the open tapered nozzle into the transverse opening a distance at least adequate to force the enlarged portion thereof into the tubular body and permit entry of the reduced diameter segment to thereby lock the flexible plastic vial to the needle assembly,
- squeezing the flexible plastic vial to dispense the contained chemical disinfectant solution into the disposable needle assembly, and
- agitating the disposable needle assembly to ensure that the chemical sterilization solution contacts all surfaces contained with said assembly.

20. The method of claim 19 wherein the volume of chemical disinfectant solution dispensed within said disposable needle assembly is equal to substantially one-half the interior volume thereof.

* * * * *